United States Patent

Woloszko et al.

[11] Patent Number: 5,741,319
[45] Date of Patent: Apr. 21, 1998

[54] BIOCOMPATIBLE MEDICAL LEAD

[75] Inventors: Jean Woloszko, Jupille, Belgium; Patrick T. Cahalan, Geleen, Netherlands; Marc Hendriks, Hoensbroek, Netherlands; Michel Verhoeven, Maastricht, Netherlands

[73] Assignee: Medtronic, Inc., Minneapolis, Minn.

[21] Appl. No.: 379,423

[22] Filed: Jan. 27, 1995

[51] Int. Cl.⁶ .......................................... A61N 1/05
[52] U.S. Cl. ............................... 607/118; 600/377
[58] Field of Search .......................... 128/642, 640; 607/116–118, 129, 130; 600/377

[56] References Cited

U.S. PATENT DOCUMENTS

| | | | |
|---|---|---|---|
| 3,738,368 | 6/1973 | Avery et al. | |
| 3,866,247 | 2/1975 | Sparks | 3/1 |
| 4,319,363 | 3/1982 | Ketharanathan | 3/1.4 |
| 4,381,007 | 4/1983 | Doss | 128/303.1 |
| 4,401,122 | 8/1983 | Clark, Jr. | 128/635 |
| 4,458,686 | 7/1984 | Clark, Jr. | 128/635 |
| 4,506,680 | 3/1985 | Stokes | 128/786 |
| 4,512,761 | 4/1985 | Raible | 604/8 |
| 4,573,481 | 3/1986 | Bullara | 128/784 |
| 4,577,642 | 3/1986 | Stokes | 128/784 |
| 4,606,118 | 8/1986 | Cannon et al. | 29/825 |
| 4,627,906 | 12/1986 | Gough | 204/415 |
| 4,670,014 | 6/1987 | Huc et al. | 604/891 |
| 4,711,251 | 12/1987 | Stokes | 128/784 |
| 4,759,757 | 7/1988 | Pinchuk | 623/1 |
| 4,798,606 | 1/1989 | Pinchuk | 623/1 |
| 4,920,979 | 5/1990 | Bullara | 128/784 |
| 4,923,380 | 5/1990 | Hue et al. | 425/68 |
| 4,955,892 | 9/1990 | Daniloff | 606/152 |
| 4,986,831 | 1/1991 | King et al. | 623/1 |
| 5,031,621 | 7/1991 | Grandjean et al. | |
| 5,085,632 | 2/1992 | Ikada et al. | |
| 5,092,332 | 3/1992 | Lee et al. | |
| 5,125,405 | 6/1992 | Schmid | 128/640 |
| 5,133,422 | 7/1992 | Coury et al. | 128/784 |
| 5,264,551 | 11/1993 | Petite et al. | 530/356 |
| 5,265,608 | 11/1993 | Lee et al. | 607/118 |
| 5,282,468 | 2/1994 | Klepinski | 607/118 |
| 5,324,312 | 6/1994 | Stokes et al. | 607/37 |
| 5,385,579 | 1/1995 | Helland | 601/130 |
| 5,413,597 | 5/1995 | Krajicek | 128/DIG. 8 |

FOREIGN PATENT DOCUMENTS

| | | |
|---|---|---|
| 9109909 | 2/1993 | France . |
| 328752 | 3/1991 | Japan . |
| 3735137 | 10/1987 | Netherlands . |
| 4028088 | 9/1990 | Netherlands . |
| 9302718 | 2/1993 | WIPO . |

OTHER PUBLICATIONS

*A Spiral Nerve Cuff Electrode for Peripheral Nerve Stimulation*, Gregory G. Naples, et al., Transactions on Biomedical Engineering, vol. 35, No. 11, Nov. 1988.

*Considerations for Safety with Chronically Implanted Nerve Electrodes*, William F. Agnew et al., Neurological Research Laboratory, Huntington Medical Research Institutes, Pasedena, California, U.S.A.

(List continued on next page.)

*Primary Examiner*—Lee S. Cohen
*Attorney, Agent, or Firm*—Michael J. Jaro; Harold Patton

[57] ABSTRACT

A medical lead having a lead body and a biocompatible cuff and especially suitable for use as a nerve electrode. In the preferred bipolar embodiment the lead body has two conductors running therethrough. The distal end is coupled to a pulse generator, the proximal end is coupled to the biocompatible cuff. The biocompatible cuff is cylindrical and is constructed from collagen. Preferably the collagen is multi-layer, i.e. the first portion is cross-linked to an amount greater than the second portion. Through such a construction the collagen promotes tissue ingrowth in the region proximate a nerve and does not permit tissue ingrowth in the region away from the nerve, e.g. the exterior of the cuff.

23 Claims, 3 Drawing Sheets

OTHER PUBLICATIONS

*Properties of Implanted Electrode for Functional Electrical Stimulation*, Dejan Popvic, Annals of Biomedical Engineering, vol. 19, pp. 303–316, 1991.

*Microtopography and Soft Tissue Response*, Craig E. Campbell, et al., Journal of Investigative Surgery, vol. 2, 1989.

*Comparison of Neural Damage Induced by Electrical Stimulation with Faradaic and Capacitor Electrodes*, D.B. McCreery, et al., Annals of Biomedical Engineering, vol. 16, pp. 463–481, 1988.

*Biocompatibility and Tissue Regenerating Capacity of Crosslinked Dermal Sheep Collagen*, Leon Olde Damink, University of Twente, Thesis.

*Prevention of Leakage of Intestinal Anastomoses with Collagen.*, G.J. de Jongh, et al. The 19th Annual Meeting of the Society for Biomaterials, Apr. 28–May 2, 1993, Birmingham, AL.

*The Study of Collagen Membrane of Guided Tissue Regeneration*, Qiqing Zhang, Institute of Biomedical Engineering, Chinese Academy of Medical Sciences, Tianjin.

*In Vivo Interactions with (Tissue Culture Pretreated) Dermal Sheep Collagen*, P.B. van Wachem et al., Mat. Res. Soc. Symp. Proc. vol. 252. 1992. Abstract.

*Collagenous Biocomposites for the Repair of Soft Tissue Injury*, David Christiansen et al., Mat. Res. Soc. Symp. Proc. vol. 252. 1992. Abstract.

*A Highly Sensitive Glucose Electrode Using Glucose Oxidase Collagen Film*, Daniel R. Thevenot, et al. Bioelectrochemistry and Bioenergetics, 548–553 (1978).

*A Glucose Electrode Using High–Stability Glucose–Oxidase Collagen Membranes*, Daniel R. Thevenot et al. Diabetes Care, vol. 5, No. 3, May–Jun. 1982.

"Application of collagen to medical electronics: Collagen electrode," by Mineo Ito and Tsuneao Okuda; *Medical Electronics and Biotechnology*, 9(5): 355–358, 1971.

"Collagen fiber electrode for recording of peripheral nerve activity," by Ryoji Yonezava and Ishio Ninomiya; *Medical Electronics and Bioengineering*, 14(5): 387–392, Oct., 1976.

BIOCOMPATIBLE MEDICAL LEAD

FIELD OF THE INVENTION

This invention relates to the field of body-implantable medical device systems, and in particular to a biocompatible medical lead which features an electrode constructed from collagen.

BACKGROUND OF THE INVENTION

Modern electrical therapeutic and diagnostic devices, such as pacemakers or nerve stimulators for example, require a reliable electrical connection between the device and the body. In cases of nerve stimulators, in particular, chronically reliable electrical connections have been difficult to attain. In a chronic setting it has been found many medical electrical leads may damage a nerve either mechanically or electrically or both.

Mechanically induced damage includes thickened epineurium due to accumulation of connective tissue between the electrode and the nerve, increased subperineural and endoneural connective tissue, endoneural edema, demyelinization, axonal degeneration and frank axonal loss. Such damage may be caused in several ways. First, if the lead and in particular the electrode which interfaces with the nerve does not move with the nerve, then abrasion may result. Second, the presence of the lead and in particular the electrode, a foreign object, may cause edema or swelling of the nerve. As the nerve swells it may be constricted by the lead. A compressive force may thereby be induced upon the nerve. In the past a so called "self-sizing" nerve electrode was fashioned to avoid such damage. Such an electrode may be seen in the U.S. Pat. No. 4,920,979 to Bullara entitled "Bidirectional Helical Electrode for Nerve Stimulation" and assigned to the Huntington Medical Research Institute. To date, however, such electrodes have not been wholly satisfactory.

Electrically induced damage may also be caused by a chronic nerve electrode. Such damage results in, among other injuries, axonal degeneration as well as nerve edema. While it has been shown that the type of electrical stimulation, e.g. frequency, waveform, amplitude, may be a significant factor, the actual electrode design may also affect the degree of electrically induced damage. In particular a medical lead which provides the optimal electrical characteristics for the desired therapy is needed.

SUMMARY OF THE INVENTION

The present invention provides a reliable biocompatible medical lead for establishing an electrical connection with a tissue of the body. The present invention is particularly suited for use as a nerve electrode and essentially comprises a lead body and a biocompatible cuff. In the preferred bipolar embodiment the lead body has two conductors running therethrough. The proximal end is coupled to a pulse generator, the distal end is coupled to the biocompatible cuff. The biocompatible cuff is cylindrical and is constructed from collagen. Preferably the collagen cuff has multiple layers. The specific characteristics of each layer may vary. For example, in the preferred embodiment the first layer has a cross-linking percentage different than the second layer. In addition, the first layer also has an average pore size different from the average pore size of the second layer. Through such a multi-layer construction the collagen cuff promotes tissue ingrowth in the region proximate the nerve and does not permit tissue ingrowth in the region away from the nerve, e.g. the exterior of the cuff. The resultant electrode, when chronically implanted, may firmly attach to the nerve but not to the surrounding tissue. In such a manner the mechanically induced damage may be minimized or even entirely eliminated. In addition, it is believed the use of collagen to electrically interface with a nerve provides superior electrical performance as compared to previously used nerve electrodes. Finally the collagen may additionally be loaded with a compound or compounds, such as a pharmaceutical, to improve its performance or biocompatibility.

BRIEF DESCRIPTION OF THE DRAWINGS

The present invention may be better understood and appreciated with reference to a detailed description of a specific embodiment of the invention, when read in conjunction with the accompanying drawings, wherein.

It should be understood the drawings are not necessarily to scale.

DETAILED DESCRIPTION OF THE INVENTION

The present invention is described within the context of a biocompatible medical lead specifically adapted for use in connection with an implantable nerve stimulator, such as the Medtronic Itrel™ as well as other models commercially available from Medtronic, Inc., Minneapolis, Minn. The present invention, however, may be advantageously practiced in conjunction with many different types of implantable medical devices as well as many other various embodiments of therapeutic or diagnostic catheters. For purposes of illustration only, however, the present invention is below described in the context of a biocompatible medical lead used for nerve stimulation.

Figure 1:
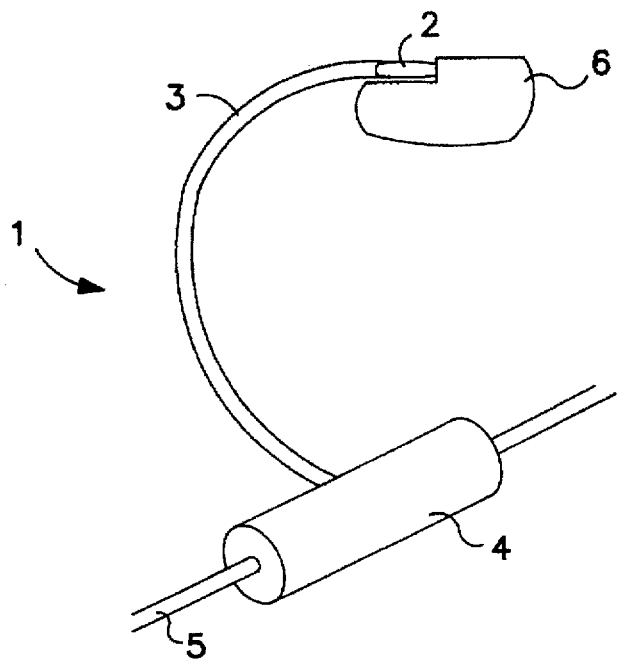
FIG. 1 is a perspective view of a nerve stimulation system featuring a biocompatible medical lead of the present invention.

Referring to FIG. 1, there is a perspective view of a lead according to the present invention. As seen lead 1 consists essentially of a connector assembly 2, lead body 3 and electrode 4. As seen electrode 4 attaches about nerve 5. Connector assembly 2 provides an electrically coupling between lead 1 and an implantable pulse generator 6. In a preferred embodiment, connector assembly 2 is constructed to meet the industry standard IS1-Bi. Of course other alternative embodiments of a connector assembly may be used, such as that described in U.S. Pat. No. 5,324,312 entitled "Tool-Less Threaded Connector Assembly" issued to Stokes, et al.

Figure 2:
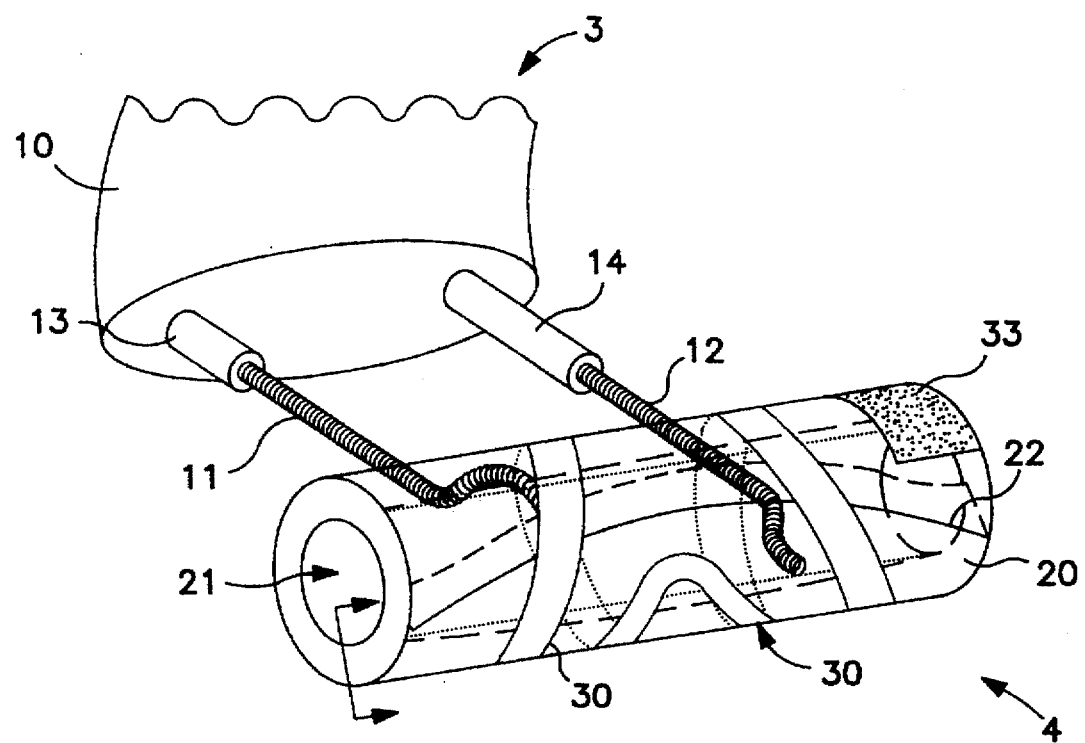
FIG. 2 is a perspective view of the electrode used in the present invention and featuring a collagen cuff.

As best seen in FIG. 2 lead body 3 consists of an outer insulative sleeve 10 housing a pair of conductors 11, 12.

Preferably each conductor 11, 12 is housed within a separate insulative covering 13, 14 which, in turn, are each housed within sleeve 10. Sleeve 10 as well as insulative coverings 13, 14 are each preferably constructed from silicone and may be surface treated according to the teachings of U.S. Pat. No. 5,133,422 entitled "Radio Frequency Glow Discharge Surface Treatment of Silicone Tubing Used as a Covering For Electrical Leads to Improve Slip Properties Thereof" incorporated herein by reference. It should be understood sleeve 10 and insulative coverings 13, 14 are shown partially cut away in FIG. 2 for clarity. In the preferred embodiment sleeve 10 and insulative coverings 13, 14 extend so that they insulate conductors 11, 12 completely between connector assembly 2 and electrode 4. Conductors 11, 12 are preferably multifilar coils constructed from a platinum-iridium alloy, although other biocompatible conductive alloys may also be used, such as MP35N. Although conductors 11, 12 are depicted as side by side, they may in addition also be configured in a coaxial manner. In addition, besides coils, conductors 11, 12 may be fashioned in other suitable forms, such as bundled wire, conductive sheets, foils, ribbons or polymers or any combination thereof.

Figure 3:
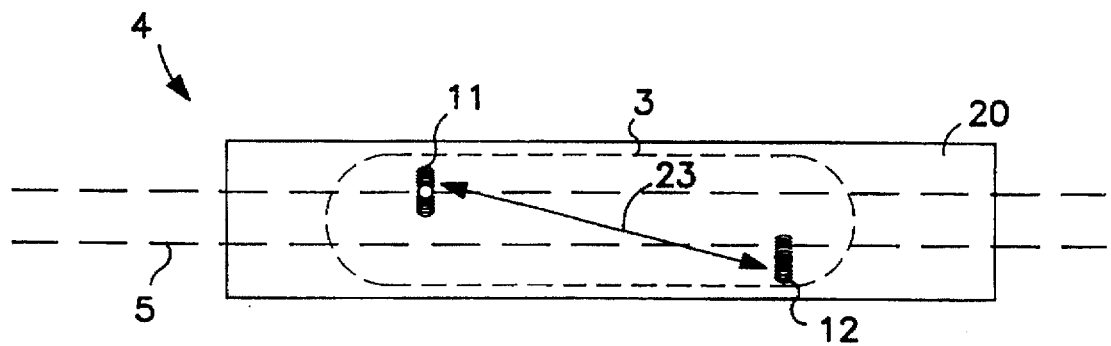
FIG. 3 is a side view of the collagen cuff used in the present invention
Figure 4:
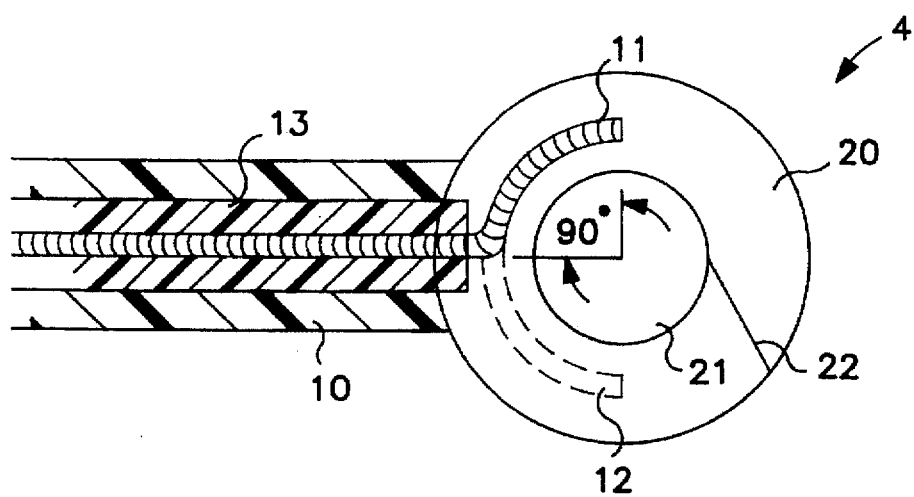
FIG. 4 is a cross-sectional view of the collagen cuff shown in FIG. 3.

Electrode 4 is constructed from conductors 11, 12 and cuff 20, as best seen in FIG. 2. Cuff 20, in the preferred embodiment, is cylindrical and has a lumen 21 therethrough. Slit 22 permits cuff 20 of electrode 4 to be positioned so nerve 5 runs through lumen 21 (not shown in FIG. 2 but seen in FIG. 1.) Conductors 11, 12 are joined within cuff 20 so they are housed and electrically exposed along the cuff over a span between 10 to 180 degrees, preferably 90 degrees as depicted in FIG. 4. As best seen in FIG. 3 conductors 11, 12 are preferably positioned so they will create a diagonal electrical field 23 about lumen 21 and nerve 5 positioned therethrough.

Cuff 20 further features a ribbon 30 wrapped thereabout to provide initial mechanical anchoring of cuff 20 to nerve 5. In particular, ribbon 30 is formed from a flattened collagen wire and fashioned into a helical shape. Ribbon 30 functions to initially maintain the position of cuff 20 around nerve 5, i.e. ribbon 30 biases cuff 20 in the position shown in FIGS. 1 and 2.

Ribbon 30 is preferably constructed from a bioabsorbable material which will degrade a short time after implant, preferably between 7 to 14 days. In particular ribbon 30 is constructed from a non-cross-linked collagen or collagen compound or from collagen having a cross-linking percentage in the range from 0–50%. Through such a construction ribbon 30 will degrade at a rate proportional to the amount of tissue ingrowth into the pores of inner portion 40. Thus once the nerve is firmly affixed by tissue ingrowth to the inner portion 40, ribbon member 30 will have been absorbed and thus no longer maintain cuff 20 around nerve 5. In the preferred embodiment ribbon 30 is constructed from bovine collagen although other types of collagen may also be used, for example porcine collagen.

Figure 5:
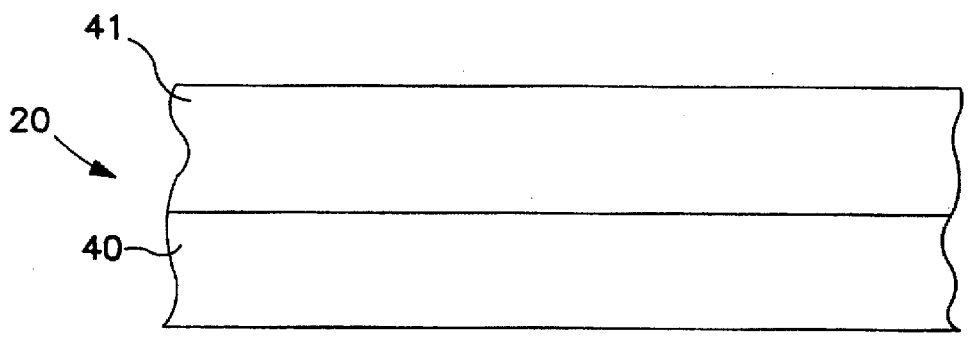
FIG. 5 is a sectional view of the collagen used in the collagen cuff showing multi-layer construction.

As discussed briefly above, the preferred embodiment of cuff 20 has a multi-layer construction, having inner layer 40 and outer layer 41, as depicted in FIG. 5. Each layer may have differing percentages of cross-linking densities or average pore size or both. Through such a construction, cuff 20 permits tissue ingrowth in the region proximate nerve 5 while remaining relatively non-reactive or slippery along its outer region.

Inner portion 40 is preferably bovine collagen which has been treated to promote tissue ingrowth by the nerve and thus "fuse" cuff 20 with the nerve. Tissue ingrowth is dependant upon both the percentage of cross-linkage of the material as well as the average pore size within the material. Inner portion 40 preferably is cross-linked in the range of 20–100% (the cross-linking percentage is calculated according to the formula described below) and has an average pore size in the range of 20–50 microns, although conceivably larger or smaller pore sizes may also be acceptable.

Outer portion 41, in contrast, is treated to not promote tissue ingrowth and thus remain relatively "slippery" and not bind with the surrounding tissue. In such a manner cuff 20 does not cause mechanical stresses to be induced upon the nerve. Outer portion 41 is constructed from a compressed collagen material cross-linked in the range of 50–100%, and has an average pore size in the range of 0–20 microns. The thickness of inner portion 40 and outer portion 41 are dependant upon the application, the size of each conductor 11, 12, as well as the stiffness of the collagen used. In the preferred embodiment each conductor 11, 12 has a coil diameter of 300 microns, inner portion 40 is 200 microns thick and outer portion 41 is 200 microns thick.

Figure 6:
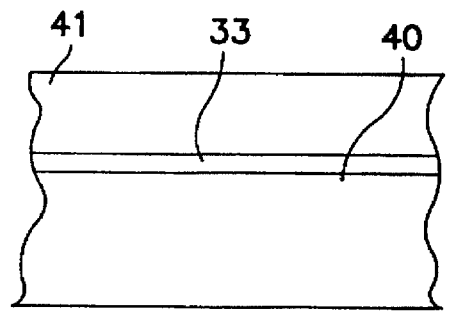
FIG. 6 is a sectional view of an alternate embodiment collagen cuff.

A further embodiment may be seen in FIG. 6, in which insulative barrier 33 is provided interiorly within cuff 20. Insulative barrier 33 comprises a thin insulative polymer having a thickness between 5–100 micrometers. Insulative barrier 33 is provided to electrically insulate the electrical interface between nerve 5 and conductors 11, 12 so as to increase the sensitivity of the electrode 4 as well as insulate the surrounding tissue from any stimulative electrical signals. In this embodiment inner portion 40 and outer portion 41 have the same characteristics as those discussed above and conductors 11, 12 are also positioned within inner portion 40. Also as discussed above, the thickness of inner portion 40 and outer portion 41 are dependant upon the application as well as the stiffness of the collagen used.

Collagen cuff 20 may be further be treated to simultaneously release a pharmaceutical agent. In particular cuff 20 may release an anti-inflammatory agent, such as the steroid dexamethasone sodium phosphate. A believed therapeutic amount may be achieved by application of a solution of 200 mg U.S.P. dexamethasone sodium phosphate dissolved in 5.0 cc isopropanol and 5.0 cc distilled or deionized water onto cuff 20. Collagen cuff 20 may also be treated alternatively to simultaneously release other pharmaceutical agents, such as a nerve growth factor or an anti-biotic, such as gentamicin.

In addition, insulative barrier 33 may also be treated to release a pharmaceutical agent. See, for example, Stokes, U.S. Pat. No. 4,506,680 and related Medtronic U.S. Pat. Nos. 4,577,642; 4,606,118 and 4,711,251.

As discussed briefly above cuff 20 is preferably constructed from collagen. In the preferred embodiment cuff 20 is constructed from bovine collagen which has been cross-linked. Other types of collagen, however, may also be used, such as pig or sheep collagen. Cross-linking may be accomplished in any acceptable manner. In the preferred embodiment cross-linking of collagen is accomplished according to the principles set forth in U.S. Pat. No. 5,264,551 entitled "Process for Cross-Linking Collagen by Diphenylphosphorylazide the Cross-Linked Collagen Obtained Thereby and Collagen Based Biomaterials Thus Cross-Linked" issued to Petite et al and assigned to Bioetica of Lyon, France.

In particular the preferred process of cross-linking collagen is of the type comprising the formation of amide bonds by means of acylazide groups and is characterized in that the collagen is reacted with diphenyl-phosphorylazide. This simplifies the collagen cross-linking process and permits one to adjust the degree of cross-linking at discretion without introducing any cross-linking agent. In particular cross-linking is accomplished with diphenylphosphorylazide (DPPA) in a non-aqueous solvent medium. Preferably, the non-aqueous solvent is constituted by dimethylformamide (DMF). The DPPA concentration is comprised between 0.0125% and 1.50% by volume/volume, and preferably still between 0.25 and 0.7%. The reaction with DPPA is carried out by incubation at an incubation temperature comprises between about 0–10 degrees Celsius, and preferably about 4 degrees Celsius, for an incubation period of between 2–24 hours, preferably 24 hours. After reacting the collagen with the DPPA, at least one rinsing with a borate buffer solution of pH 8.9 is carried out to eliminate the DPPA, then the collagen containing the acylazide groups is introduced in a solution of borate buffer having a pH about equal to 8.9 and incubated at a temperature comprised between about 0–10 degrees Celsius, and better still about 40 degrees Celsius, for an incubation period of between 2–24 hours, preferably 24 hours.

For example, to cross-link a collagen film with DPPA may be accomplished as follows: A gel is prepared from calf skin washed and pared off beforehand with a mixture of lime and sulphide. The skin is then neutralized, then the salts are eliminated by two washes in water. The skin is then ground, and washed with phosphate buffer of pH 7.8 (potassium dihydrogeno-phosphate 0.78 g/l and disodic monohydrogenophosphate 21.7 g/l). The phosphate is thereafter eliminated by two successive washes with ion-exchanged water. The ground material is then acidified with an acetic acid solution at 10%, the quantity of acetic acid being 5% with respect to collagen. The ground material is then kneaded until a homogeneous paste is obtained. This paste is then diluted to obtain a gel having a collagen concentration of 0.7%. The gel is then placed in small Teflon molds, and allowed to evaporate. The resulting film is thereafter cut with a punch into pellets of 1 sq. cm.

Cross-linking the resulting collagen film may be accomplished as follows: Four pellets (quantity for purposes of illustration) of films of surface 1 sq. cm. are incubated for 24 hours at 4 degrees Celsius in 10 ml of a solution of DMF containing 0.25% of DPPA (concentration expressed in volume/volume). The DPPA is then removed from the film by rinsing with 10 ml of DMF solution. The DMF is then eliminated by rinsing with 10 ml of a borate buffer solution of pH 8.9 (sodium tetraborate 0.04M, boric acid 0.04M). Finally, the films are incubated for one night in a borate buffer of pH 8.9. They are then drained on a filter-paper, and dried in the open. They can afterwards be sterilized, for example with gamma rays or ethylene oxide.

The degree of cross-linking of the collagen is measured by scanning calorimetric analysis. This technique consists in measuring, during a linear rise in temperature, the difference of energy to be supplied to the sample and to a reference in order to keep them at an identical temperature. When the collagen is denatured, a heat absorption peak appears on the recorder. The beginning of denaturation temperature (TD), the peak of denaturation temperature (TP) and the end of denaturation temperature (TF) are defined in this way.

The following calculation is made in order to calculate a collagen cross-linking percentage R:

$$R=((TX-TI)\div(TM-TI))\times 100$$

TM: maximum denaturation temperature which it is possible to obtain when cross-linking collagen with DPPA; in fact, in the present case, it corresponds to the temperature obtained with an 0.75% DPPA concentration ([DPPA]).

TI: temperature of denaturation obtained on the non-treated tissue.

TX: temperature of denaturation obtained on the tissue with a DPPA concentration X.

Figure 7:
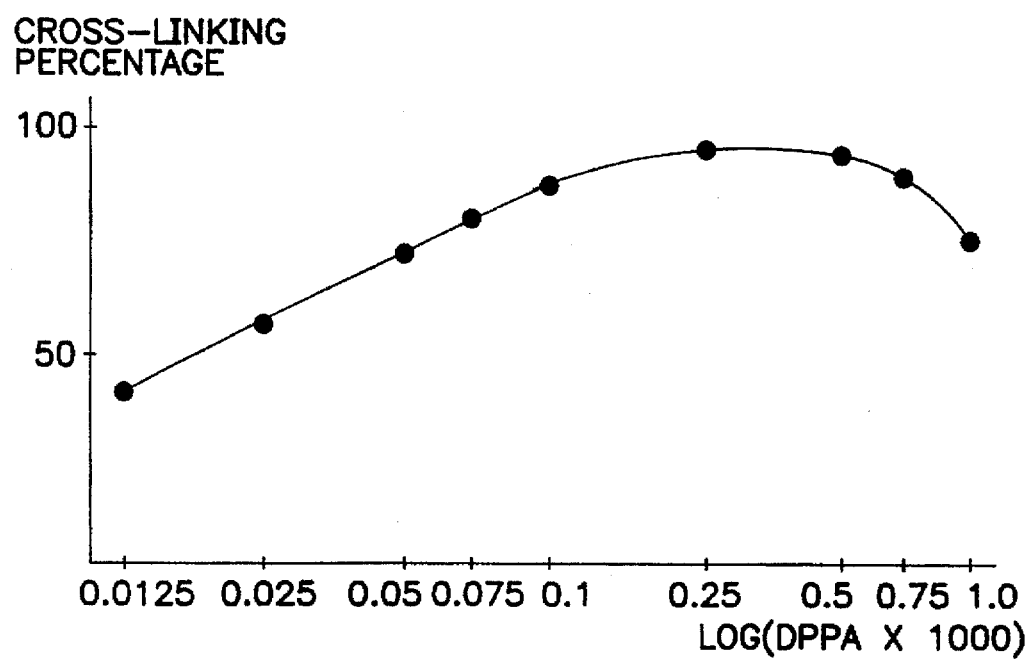
FIG. 7 represents the evolution of the collagen cross-linking percentage, called RTP, measured from the collagen denaturation peak temperature (TP) on collagen films as a function of the DPPA concentration.

R is the cross-linking % calculated from TP, the denaturation peak temperature, and is called RTP. The evolution of the RTP as a function of the Log ([DPPA]×1000) as seen in FIG. 7 is calculated as described above. In this way it has been shown between 0.0125% and 0.10%, the evolution of the RTP as a function of the Log ([DPPA]×1000) is linear. A maximum cross-linking is obtained with DPPA concentrations of 0.25%–0.5%.

Although a specific embodiment of the invention has been disclosed, this is done for the purposes of illustration and is not intended to be limiting with regard to the scope of the invention. It is contemplated that various substitutions, alterations, and/or modifications, including but not limited to those specifically discussed herein, may be made to the disclosed embodiment of the invention without departing from the spirit and scope of the invention as defined in the appended claims, which follow. For example, other methods of cross-linking collagen or types of collagen may be used. Moreover, while the invention has been described as featuring a cylindrical collagen cuff, it should be understood various other shapes and designs of the collagen cuff may be utilized, such as a helical collagen cuff or a crenelated collagen cuff. Finally, although the invention has been described in the particular context of a bipolar nerve electrode, it may further be incorporated in various other types of medical leads, including unipolar or multipolar leads as well as cardiac pacing and defibrillation leads, and still be within the scope and spirit of the claimed invention.

What is claimed is:

1. A system for stimulating body tissue comprising:
   a pulse generator;
   a conductor having a first end and a second end, the conductor covered between the first end and the second end by an insulator, the first end connected to the pulse generator;
   a biocompatible member, wherein the biocompatible member is a cuff, the second end of said conductor connected to the biocompatible member, the biocompatible member constructed from collagen, the member further having a first layer and a second layer, the first layer cross-linked to a first percentage and the second layer cross-linked to a second percentage, whereby the second layer is interior of the first layer, the second layer adapted to be positioned adjacent a body tissue to be stimulated wherein the cuff further comprises a ribbon member biasing the cuff into a first position.

2. The system according to claim 1 wherein the cuff has a center lumen therethrough.

3. The system according to claim 1 wherein the cuff has a third layer, the third layer located next to the first layer.

4. The system according to claim 3 wherein the third layer is an insulative barrier.

5. The system according to claim 4 wherein the insulative barrier is disposed between the first layer and the second layer of the cuff.

6. The system according to claim 3 wherein the third layer has means for eluting a therapeutic agent.

7. The system according to claim 1 wherein the first layer has means for eluting a pharmaceutical agent.

8. The system according to claim 7 wherein the first layer has an average pore size in the range of 0–20 microns, the second layer has an average pore size in the range of 20–50 microns.

9. The system according to claim 1 wherein the first layer is cross-linked in the range of 50-100%.

10. The system according to claim 1 wherein the second layer is cross-linked in the range of 20-100%.

11. A system for stimulating body tissue comprising:
a pulse generator;
a conductor having a first end and a second end, the conductor covered between the first end and the second end by an insulator, the first end connected to the pulse generator;
a biocompatible member, the biocompatible member further comprises a ribbon member disposed about an exterior of the biocompatible member, the ribbon member biasing the biocompatible member into a first position, the second end of said conductor connected to the biocompatible member, the biocompatible member constructed from collagen, the member further having a first layer and a second layer, the first layer having an average pore size in a first amount, the second layer having an average pore size in a second amount, whereby the second layer is interior of the first layer, the second layer adapted to be positioned adjacent a body tissue to be stimulated.

12. The system according to claim 11 wherein the first layer has an average pore size in the range of 0-20 microns.

13. The system according to claim 11 wherein the second layer has an average pore size in the range of 20-50 microns.

14. The system according to claim 11 wherein the first layer is cross-linked in the range of 50-100% and the second layer is cross-linked in the range of 20-100%.

15. A biocompatible medical lead comprising:
a first conductor having a first end and a second end;
means for connecting the conductor first end to a pulse generator;
an insulative sheath insulating the conductor between the first end and the second end;
a cylindrical collagen member coupled to the first conductor second end, the member having a center lumen therethrough, the member cross-linked in the range of 50-100%; and
a ribbon member disposed about the exterior of the cylindrical collagen member, biasing the cylindrical collagen member into a first position, the ribbon member constructed from collagen cross-linked in the range from 0-50%,.

16. The biocompatible medical lead according to claim 15 wherein the cylindrical collagen member has an inner layer, the inner layer cross-linked in the range of 20-100%.

17. The biocompatible medical lead according to claim 16 wherein the cylindrical collagen member has an average pore size in the range of 0-20 microns, the inner layer has an average pore size in the range of 20-50 microns.

18. A biocompatible medical electrode comprising:
a collagen member having a central lumen;
a first conductor coupled to the member, the first conductor extending around the central lumen in a first direction for a radial distance of between 10-180 degrees; and
a second conductor coupled to the member, the second conductor extending around the central lumen in a second direction for a distance of between 10-180 degrees, the second conductor longitudinally spaced from the first conductor wherein the collagen member has a first layer and a second layer, the first layer cross-linked to a first percentage and the second layer cross-linked to a second percentage wherein the first percentage is different from the second percentage.

19. The biocompatible medical electrode according to claim 18 wherein the first percentage is in the range of 50-100%.

20. The biocompatible medical electrode according to claim 18 wherein the second percentage in the range of 20-100%.

21. A biocompatible medical electrode comprising:
a collagen member having first layer, a second layer and a central lumen, the first layer has an average pore size of a first amount, the second layer has an average pore size of a second amount, wherein the first amount is in the range of 0-20 microns and the second amount is in the range of 20-50 microns;
a first conductor coupled to the member, the first conductor extending around the central lumen in a first direction for a radial distance of between 10-180 degrees; and
a second conductor coupled to the member, the second conductor extending around the central lumen in a second direction for a distance of between 10-180 degrees.

22. A biocompatible medical lead comprising:
a lead body, the lead body comprising a first conductor having a first end and a second end, the first end having means for electrically coupling with a pulse generator
the first conductor covered between the first end and the second end by an insulative barrier; and
a biocompatible member connected to the second end of the first conductor, the biocompatible member constructed from collagen, the member further having a first layer and a second layer, the first layer cross-linked a first percentage, the second layer cross-linked a second percentage, the first percentage is different from the second percentage, whereby the second layer is adapted to be positioned adjacent body tissue and wherein the first layer as an average pore size of a first amount, the second layer has average pore size of a second amount, the first amount is different from the second amount.

23. A biocompatible medical lead comprising:
a biocompatible member
a lead body, the lead body comprising a first conductor having a proximal end and a distal end, the proximal end having means for electrically coupling with a pulse generator, the distal end connected to the biocompatible member;
a second conductor having a proximal end and a distal end, the proximal end having means for electrically coupling with a pulse generator, the distal end connected to the biocompatible member, the first and the second conductors covered between each their respective proximal end and the distal end by an insulative barrier;
wherein the biocompatible member is constructed from collagen and has a center lumen therethrough, the member further having a first layer and a second layer, the first layer having an average pore size of a first amount, the second layer having an average pore size of a second amount, the first amount is different from the second amount whereby the second layer is adapted to be positioned adjacent body tissue.

* * * * *